US009232805B2

(12) United States Patent
Asfaw et al.

(10) Patent No.: US 9,232,805 B2
(45) Date of Patent: Jan. 12, 2016

(54) IN-SITU FORMING HYDROGEL WOUND DRESSINGS CONTAINING ANTIMICROBIAL AGENTS

(75) Inventors: Bruktawit T. Asfaw, Mableton, GA (US); John C. Jackson, Rancho Cucamonga, CA (US); Zhihua Lu, Johns Creek, GA (US); Xiaowen Zhai, Alpharetta, GA (US); Sameer Shums, Plano, TX (US); Thomas Hirt, Rebstein (CH); Xianbo Hu, Alpharetta, GA (US); Claude-Raymond René, Atlanta, GA (US)

(73) Assignee: BIOCURE, INC., Norcross, GA (US)

( * ) Notice: Subject to any disclaimer, the term of this patent is extended or adjusted under 35 U.S.C. 154(b) by 752 days.

(21) Appl. No.: 13/135,247

(22) Filed: Jun. 28, 2011

(65) Prior Publication Data
US 2012/0009275 A1 Jan. 12, 2012

Related U.S. Application Data

(60) Provisional application No. 61/398,679, filed on Jun. 29, 2010.

(51) Int. Cl.
*A01N 59/16* (2006.01)
*A01P 1/00* (2006.01)
*A01N 25/04* (2006.01)
*A61F 13/00* (2006.01)

(52) U.S. Cl.
CPC ............. *A01N 59/16* (2013.01); *A01N 25/04* (2013.01); *A61F 2013/0011* (2013.01)

(58) Field of Classification Search
None
See application file for complete search history.

(56) References Cited

U.S. PATENT DOCUMENTS

| | | | |
|---|---|---|---|
| 4,495,168 A | 1/1985 | Schmolka | |
| 5,047,055 A | 9/1991 | Bao et al. | |
| 5,278,202 A | 1/1994 | Dunn et al. | |
| 5,326,567 A | 7/1994 | Capelli | |
| 5,344,452 A | 9/1994 | Lemperle | |
| 5,410,016 A | 4/1995 | Hubbell et al. | |
| 5,490,984 A | 2/1996 | Freed | |
| 5,508,317 A | 4/1996 | Muller | |
| 5,514,379 A | 5/1996 | Weissleder et al. | |
| 5,529,914 A | 6/1996 | Hubbell et al. | |
| 5,709,854 A | 1/1998 | Griffith-Cima et al. | |
| 5,804,213 A | 9/1998 | Rolf | |
| 5,844,016 A | 12/1998 | Sawhney et al. | |
| 5,879,713 A | 3/1999 | Roth et al. | |
| 5,902,599 A | 5/1999 | Anseth et al. | |
| 5,932,674 A | 8/1999 | Muller | |
| 5,942,209 A | 8/1999 | Leavitt et al. | |
| 5,981,826 A | 11/1999 | Ku et al. | |
| 6,007,833 A | 12/1999 | Chudzik et al. | |
| 6,028,164 A | 2/2000 | Loomis | |
| 6,037,366 A | 3/2000 | Krall et al. | |
| 6,060,534 A | 5/2000 | Ronan et al. | |
| 6,083,524 A | 7/2000 | Sawhney et al. | |
| 6,129,761 A | 10/2000 | Hubbell | |
| 6,146,373 A | 11/2000 | Cragg et al. | |
| 6,150,581 A * | 11/2000 | Jiang et al. ............ 602/50 |
| 6,152,943 A | 11/2000 | Sawhney | |
| 6,153,211 A | 11/2000 | Hubbell et al. | |
| 6,166,130 A | 12/2000 | Rhee et al. | |
| 6,179,862 B1 | 1/2001 | Sawhney | |
| 6,191,193 B1 | 2/2001 | Lee et al. | |
| 6,201,065 B1 | 3/2001 | Pathak et al. | |
| 6,265,509 B1 | 7/2001 | Muller | |
| 6,652,883 B2 | 11/2003 | Goupil et al. | |
| 6,676,971 B2 | 1/2004 | Goupil et al. | |
| 6,710,126 B1 | 3/2004 | Hirt et al. | |
| 7,070,809 B2 | 7/2006 | Goupil et al. | |
| 7,118,761 B2 | 10/2006 | Canada et al. | |
| 2002/0122771 A1* | 9/2002 | Holland et al. ............ 424/43 |
| 2005/0266081 A1 | 12/2005 | Rogozinski | |
| 2008/0063693 A1* | 3/2008 | Cook et al. ............ 424/443 |

FOREIGN PATENT DOCUMENTS

| | | |
|---|---|---|
| EP | 0174849 | 3/1986 |
| EP | 0560014 | 9/1993 |
| EP | 0610056 | 8/1994 |
| EP | 0730847 | 9/1996 |
| EP | 1825841 | 9/2007 |
| WO | 9509659 | 4/1995 |
| WO | 9722371 | 6/1997 |
| WO | 9722372 | 6/1997 |
| WO | 9817200 | 4/1998 |
| WO | 9817201 | 4/1998 |
| WO | 9903454 | 1/1999 |
| WO | 9912577 | 3/1999 |
| WO | 9944643 | 9/1999 |
| WO | 0009087 | 2/2000 |
| WO | 0009088 | 2/2000 |
| WO | 0009190 | 2/2000 |
| WO | 0009199 | 2/2000 |
| WO | 0023054 | 4/2000 |
| WO | 0035373 | 6/2000 |
| WO | 0050103 | 8/2000 |
| WO | 0062827 | 10/2000 |
| WO | 0064977 | 11/2000 |
| WO | 0116210 | 3/2001 |
| WO | 0117574 | 3/2001 |
| WO | 0144307 | 6/2001 |
| WO | 0155360 | 8/2001 |
| WO | 0168722 | 9/2001 |
| WO | 0170132 | 9/2001 |
| WO | 0170289 | 9/2001 |
| WO | 0170290 | 9/2001 |
| WO | 0170291 | 9/2001 |
| WO | 0216443 | 2/2002 |

* cited by examiner

Primary Examiner — Sue Liu
Assistant Examiner — Erin Hirt
(74) Attorney, Agent, or Firm — Parks Woods LLC; Colleen A. Beard, Esq.

(57) ABSTRACT

A composition comprising a macromer that can be in situ polymerized into a hydrogel wound dressing directly on a wound and one or more antimicrobial agents intended to achieve bacteriostasis and/or be bacteriocidal. The antimicrobial agent is released upon application and trapped in the hydrogel upon its formation and also released over a period of time into the wound.

9 Claims, 3 Drawing Sheets

IN-SITU FORMING HYDROGEL WOUND DRESSINGS CONTAINING ANTIMICROBIAL AGENTS

CROSS REFERENCE TO RELATED APPLICATION

The present application is related to and claims priority to U.S. Provisional Application Ser. No. 61/398,679 filed on Jun. 29, 2010, the entire contents of which are incorporated herein by reference.

FIELD OF THE INVENTION

The present invention is generally in the field of wound dressings. More specifically, the present invention is directed to in situ forming hydrogel wound dressings that deliver antimicrobial agents and optionally other active agents to the wound both upon application and over a period of time.

BACKGROUND OF THE INVENTION

Wounds are generally categorized as either acute injuries such as trauma, surgical wounds, burns, abrasions, avulsions, or as chronic wounds such as diabetic ulcers, venous stasis ulcers, and chronically infected wounds. In either instance, wounds require an appropriate wound dressing for protection from further injury, foreign debris, and infection and for enhancement of the healing process. There is a well documented need for a better wound dressing that is capable of addressing the multiple facets of wounds, especially chronic wounds, and ensuring that patient comfort is maintained. There is also an unmet need for more user friendly wound dressings.

Desirable characteristics of effective wound dressings vary depending upon the type of wound to be treated but generally include that they are moist, sterile, able to manage wound exudates, able to conform to the wound topography (be flexible), and able to adhere to the surrounding tissue but also be easily removed to prevent re-injury of the wound bed. Additionally, an effective wound dressing should provide mitigation for infection or the likelihood of infection.

The potential for developing a wound infection depends on many factors such as the cause of injury in acute wounds, migration of bacteria from intact skin to compromised skin in surgical wounds, and infections that develop from the lack of an effective barrier. It is thought that unresolved infections are the primary culprit for wounds that transition from acute to chronic.

When the integrity and protective function of the skin is breached, different cells migrate to the wound, starting the inflammatory response for healing the wound. This inflammatory response can be visualized at the macro level by redness, pain, and swelling. Infections from bacteria, viruses, and fungi are known to delay the wound healing process because the body first must fight the infection before it can heal itself. The risk of infection depends on the patient's condition as well as extrinsic factors such as post-operative/wound care, environment, and treatment. Since infection stems from many sources, is hard to predict the occurrence of an infection and the type of infection, which confounds the treatment options and methods. The prevention of wound infection is a primary management objective for healthcare practitioners.

In order to reduce infection and the possibility of infection, a wound dressing can include antimicrobial agents. One agent that has been used successfully is silver. Silver works as an antimicrobial agent through a number of pathways. It acts on the cell wall to inhibit cell wall replication. Silver can also inactivate the cellular respiratory chain and block the energy supply of cells, or directly act on nucleic acids such as RNA and DNA. Without those functions, the bacterium is inhibited from replication and effectively killed. This method of action is also ideal for preventing strong strains of bacteria with resistance. Because silver affects so many different functions of the microbial cell, it is nonselective, resulting in antimicrobial activity against a broad spectrum of medically relevant microorganisms including bacteria (both gram positive and gram negative strains), fungi, and yeasts. Silver is also more efficient than traditional antibiotics because it is extremely active in small quantities. For certain bacteria, as little as one part per billion of silver may be effective in preventing cell growth.

Hydrogel dressings have been proven effective in facilitating the repair of pressure ulcers, diabetic ulcers, and burns in addition to acute wounds such as cuts, scrapes and surgical wounds. A hydrogel is a network of polymer chains that are dispersed in water. The water content in a hydrogel can be adjusted within a wide range so they can be moist, if desired, or more absorbent and able to handle wound exudates. Hydrogels can possess a degree of flexibility that is very similar to natural tissue. Active agents can be directly and easily loaded into the hydrogel matrix. In addition, hydrogels do not require pre-wetting and have supplanted saline moistened gauze for many applications. Hydrogels can adhere to the intact skin without sticking directly to the injury or wound bed. A hydrogel based wound dressing can be transparent, offering the additional advantage of allowing direct visualization of the wound bed. Hydrogels can be preformed or in situ formed. Application of a composition that forms a hydrogel in situ on the wound site offers a significant advantage over a preformed hydrogel because it results in a dressing that conforms to the surface of the wound and may be used to help quantify the healing rate of the wound based upon volumetric comparison of the dressing.

SUMMARY OF THE INVENTION

A composition is provided consisting primarily of a macromer that can be in situ polymerized into a hydrogel wound dressing directly on a wound and one or more antimicrobial agents intended to achieve bacteriostasis and/or be bacteriocidal. The antimicrobial agent is trapped in the hydrogel upon its formation and then released over a period of time into the wound. The sterile liquid composition is supplied in two parts, one or both of which can contain the macromer, which are delivered onto the wound in either a spray or stream manner, whereupon they combine and polymerize immediately to form the hydrogel wound dressing. Optionally other active agents such as pain relief agents and wound healing promoting factors may be added in the pre-polymer component. Maintaining segregation of the parts ensures that the active ingredients are kept viable during the shelf life of the product and effective once delivered onto the wound bed.

By immediately forming the hydrogel dressing when applied, the method of forming a wound dressing is fast, clean, "touchless" (hands free) and simple. A single embodiment of the composition, applied to the wound either via a stream or spray application, can be applied to any size or type of wound using the same device, thereby reducing the need to prepare various sizes of pre-formed wound dressings. Because it forms in situ, the dressing is highly conformal to the wound which ensures that the active agents are more efficiently delivered directly to the wound site. Meanwhile, penetration of the hydrogel into the wound bed may aid in debridement of the wound during dressing changes without removal of epithelial cells, which is known to accelerate the wound healing process. The spray and stream application method for the wound dressing can be advantageous depending on the wound etiology, and the cavernous nature of some wounds.

The macromer is a water soluble synthetic polymer made by functionalizing water soluble polyvinyl alcohol (PVA). PVA macromer in water is unstable under common sterilization and storage conditions. The composition thus includes means to stabilize the compositions prior to application. The PVA macromer is optimized by molecular weight, acetate content, and functional group content for the particular intended type of wound to be dressed. These factors significantly affect viscosity, water uptake ability, hydrogel forming rate, adhesion, and mechanical properties of the hydrogel. A pure PVA hydrogel tends to dry out over a few hours, and this drying leads to a significant shrinkage and property changes of the hydrogel dressing. Therefore, the composition also desirably contains moisturizers.

The macromers are preferably crosslinked using a $H_2O_2$/Fe(II) redox free radical initiation system. The reducing agent and oxidizing agent are separately packaged in the two composition parts, either or both of which can contain macromer.

In one embodiment, the hydrogel contains silver chloride as the antimicrobial agent. The silver chloride is formed in situ on the wound, which results in both immediately released silver ions and silver chloride but also insoluble silver chloride, which then releases silver ions from the hydrogel over time. Silver chloride is formed in situ in the hydrogel by supplying silver, for instance in the form of silver nitrate in one part of the formulation; and chloride, such as in the form of sodium chloride in the second part. Upon delivery, the silver ions combine with the chloride ions to form insoluble silver chloride particles which are uniformly distributed in the hydrogel. The in situ formed silver chloride particles act as a reservoir of silver ions and continuously release antimicrobial silver ions for up to several days. Even a small amount of silver provides, at a minimum, bacteriostatic action. Moreover, the silver ion is released into the wound for long-lasting bactericidal effect in a controlled fashion. The positively charged ionic form is highly toxic for microorganisms but has low toxicity for human tissue cells. The dressing can be left in place for several days without replacement.

In another embodiment, in situ formed silver sulfadiazine is the antimicrobial source. One part of the formulation contains silver ions such as from silver nitrate; the other part contains sulfadiazine. Upon delivery the silver ions combine with sulfadiazine to form insoluble silver sulfadiazine particles that act as a reservoir and continuously release antimicrobial silver ions.

Another embodiment of the hydrogel wound dressing contains a combination of active agents, such as both antimicrobial silver and lidocaine. Silver ions are supplied from one part of the formulation; the other part includes lidocaine HCl. Other optional additives include haemostatic agents and growth factors.

DETAILED DESCRIPTION OF THE PREFERRED EMBODIMENTS

Figure 1:
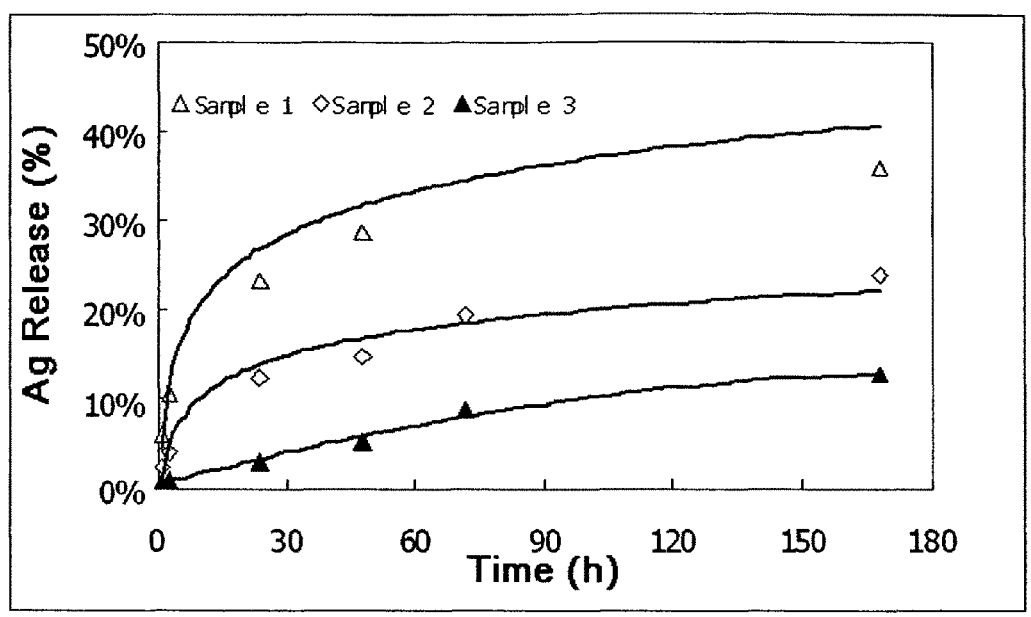
FIG. 1 illustrates silver release from one embodiment of the wound dressing.

Compositions useful for forming hydrogel wound dressings in situ are disclosed. The compositions include a macromolecular monomer (termed herein a "macromer") that forms a hydrogel. The hydrogel is formed in situ on the wound surface using a free radical initiation system or redox reaction.

In a preferred embodiment, the hydrogel is formed from macromers that are polymerized using a redox system. The reducing component includes the macromer and a reducing agent, with optionally a stabilizer and other additives. The oxidizing component includes the macromer and an oxidizing agent, with optionally a stabilizer and other additives. Both components are solutions.

The two component formulation is applied to a wound by a spray or stream from a syringe, pump, spray nozzle, or aerosol device. The two components are desirably mixed through a static mixer and delivered onto the wound. A combination of the spray and stream may be applied in a method similar to a shower head, whereby multiple streams provide the simulated broad coverage of a spray application. The macromers and other additives are sprayed or streamed onto the wound whereupon they crosslink in situ to form the hydrogel-based wound dressing.

The composition further includes one or more antimicrobial agents. The antimicrobial agent or agents will become trapped in the hydrogel upon its formation and will be released from the hydrogel both immediately and over a period of time. In a preferred embodiment, the antimicrobial agent is silver chloride, which is formed in situ as the hydrogel is formed, through the delivery and mixing of silver nitrate from one part of the composition and calcium chloride from the other part.

The invention further provides hydrogel wound dressings formed in situ on a wound that deliver one or more antimicrobial agents both immediately and over a period of time.

DEFINITIONS

The term "wound" as used herein refers to all types of tissue injuries, including those inflicted by surgery and trauma, including burns, as well as injuries from chronic medical conditions, such as atherosclerosis, vascular disease, or diabetes. The compositions described herein are useful for treatment of all types of wounds, including wounds to internal and external tissues. The wound dressings are intended to treat the various etiologies of wounds that affect the three layers of the skin—the epidermis, dermis, and subcutaneous layers.

The term "hydrogel" as used herein refers to a material having an aqueous phase with an interlaced polymeric component, with at least 10% and up to 95% of its weight as water.

The term "antibacterial" as used herein refers to both bacteriostatic agents, which inhibit growth and reproduction of bacteria without killing them, and to bactericidal agents which kill bacteria.

The term "antimicrobial" as used herein refers to a substance that kills or inhibits the growth or reproduction of microorganisms such as bacteria, fungi, yeast, or protozoans.

The term "solution" as used herein refers to solutions, suspensions, or dispersions, unless otherwise stated.

The term "spray" as used herein refers to an atomized composition, such as comprised of small or large liquid droplets, such as applied through an aerosol applicator or pump spray applicator for the intended purpose of delivering a broad application of the composition. This application method may be more suitable for superficial wounds, burns, skin grafts, and skin abrasions that cover a large area.

The term "stream" as used herein refers to a continuous, direct, and focused application of the composition. This application method may be best suited to deep wounds requiring a larger volume of hydrogel to protect the wound bed and encourage the healing process.

Designing In Situ Forming Hydrogel Wound Dressings

It should be understood that desired characteristics of a wound dressing will vary depending upon the intended usage of the dressing—such as where it will be applied, what type of wound is being treated, and other factors. However, some general characteristics can be stated.

The in situ formed dressing should be conformable and compliant so that it conforms to the topography of the wound and the tissue surface around the wound and is comfortable to wear. Conformability will also extend the longevity of the dressing. The dressing is also preferably strong enough that it can be peeled off the wound without reinjuring the wound bed and can be removed in one cohesive unit leaving little material behind in the wound bed. In some cases it is desirable to debride the wound in order to enhance overall healing. In other cases debridement is not desirable. The amount of debridement facilitated by the dressing is, in part, dependent on the degree to which the gel adheres to the wound surface. Thus, it is often desirable to control the adhesion and surface tackiness of the dressing. This can be achieved by modifying the macromer with hydrophilic or hydrophobic side chains, including an additional monomer, or adding specific additives such as surfactants, organic solvents, or amphiphilic block copolymers (e.g. pluronics).

Adhesion is the force responsible for ensuring dressing contact with the target wound site and periwound area. Preferred values for adhesion range from about 0.5N-5N (0.111 bf-1.121 bf).

Adhesion of the base dressing to a given substrate increases over time as a function of water vapor release, achieving adhesion values of over 3N at 4 hours. However an adequate initial adhesion is highly desirable as the dressing goes through a "tack" phase in which the air exposed portion of the dressing becomes very tacky or sticky.

Tack is a measure of the surface adhesion of the wound dressing. It is preferred if the tack value does not exceed 2N (0.451 bf). Tack can be measured after the dressing is formed on the skin and has completely cured. The tack phase can onset as soon as 5 minutes after application and persist for as long as 4 hours, depending upon the dressing's chemical make-up and environmental factors such as temperature and humidity. Tack is a consistent characteristic of the in-situ curing PVA dressing. Temperatures greater than 37° C. encourage faster moisture release creating a shorter tack phase whereas in high humidity or cool environments the dressing retains moisture, extending the tack phase. Decreasing the tack has the advantage of increasing the efficacy of the dressing by reducing the chance of accidental adhesion failure to the target wound site due to tack interactions with other surfaces.

Other important characteristics of a wound dressing are its moisture handling characteristics. It may be desirable for the wound dressing to absorb wound exudates in an effort to maintain a moist environment to promote healing without causing maceration. The amount of moisture that can be absorbed by the wound dressing can be manipulated by adjusting the composition and controlling the swelling ability. In an effort to preserve the moisture absorption of the dressing, the wound dressing should also allow for water transmission and a degree of evaporation from the top surface of the dressing. This evaporation rate provides the appropriate counter-balance to the moisture absorbed from the wound bed. Accordingly, moisture handling characteristics include moisture uptake and MVTR, the moisture vapor transmission rate or the rate at which water vapor escapes through a substrate. Preferred values for moisture uptake range from about 20 to 40% in the first 24 hours of application. Preferred values for MVTR range from about 100-400 grams per square meter in the first 24 hours of application.

The fluid absorption of the wound dressings can be manipulated in a variety of ways. Experimentation has shown that the absorption is greater for dressings with lower (3-8%) PVA solids than dressings with higher (10-20%) PVA solids. The addition of chemical ingredients can also greatly increase the dressing's fluid absorption. AMPS (2-Acrylamido-2-methylpropane sulfonic acid) for example can be attached to the acryl amide portion of the PVA backbone and its open hydrophilic sulfonic portion makes the dressing itself hydrophilic. Through PVA solids and chemical additives the hydrogel dressing can be manipulated to absorb greater than 100% of its original weight. However, a significant change in the volume and morphology of the dressing can lead to undesired physical property breakdown. Accordingly, the moisture handling capability has to be catered in order to keep the dressing functional and effective.

The hydrogel dressing additionally needs to be safe and stable. All of the composition ingredients should be biocompatible or non-irritant in the amounts present in the final hydrogel dressing. The composition should be sterile and able to preserve the activity of drug.

The viscosity of the composition should be suitable for the delivery method. The viscosity should be controlled so that the composition can be sprayed or streamed onto the wound in a way that a conformal wound dressing is generated. Viscosity can be controlled by changing the molecular weight and concentration of the macromer.

Gelation of the macromer composition on the wound is preferably rapid, to avoid run off of the composition from the place of application. The gelling time can be 5 minutes or less, preferably less than about three minutes, more preferably less than about 0.5 minute, and, in some situations, as low as about 10 seconds or less. The gelling time is controlled by adjusting the concentration of initiators, type of initiator, crosslinking group of the PVA macromer, solids content of the composition, and mixing mechanism.

The dressing will be required to provide at a minimum bacteriostatic and fungistatic activity antimicrobial activity. It is possible to create a bacteriocidal effect by adjusting the concentration of the active ingredient. The antimicrobial effect is designed to be maintained for the first 24 hours of application and following that time period, the wound dressing will act as a barrier to prevent reinfection of the wound area. The silver chloride loading within the dressing can range between 25 ppm to 2000 ppm with gradually increasing cidal effect.

Components of the Composition

The composition includes a PVA macromer that can quickly crosslink after delivery, to form a hydrogel dressing on a wound. The composition further includes aqueous media, redox components, stabilizers for the redox components, and one or more antimicrobial agents or pre-antimicrobial agents, and may include additives such as an absorbent, and other active agents.

PVA Macromer:

The macromer can be made by general synthetic methods known to those skilled in the art. The preferred macromers can be made as described in U.S. Pat. Nos. 5,508,317, 5,665,840, 5,807,927, 5,849,841, 5,932,674, 5,939,489, and 6,011,077. The macromer has at least two pendant chains containing groups that can be crosslinked. The term "group" includes single polymerizable moieties containing vinyl group such as an acrylate, acrylamide. The crosslinkers are desirably present in an amount of from about 0.01 to 10 millimole of crosslinker per gram of backbone (mmol/g), more desirably about 0.05 to 1.0 mmol/g. The macromer can contain more than one type of crosslinkable group. The pendant chains are attached via the hydroxyl groups of the backbone. Desirably, the pendant chains having crosslinkable groups are attached via cyclic acetal linkages to the 1,2-diol or 1,3-diol hydroxyl groups. Desirable crosslinkable groups include (meth)acrylamide, (meth)acrylate, styryl, vinyl ester, vinyl ketone, and vinyl ethers. Particularly desirable are ethylenically unsaturated functional groups. A particularly desirable crosslinker is N-acryloyl-aminoacetaldehyde dimethylacetal (NAAADA) in an amount from about 1 to 500 crosslinkers per macromer. A particularly preferred macromer has a PVA backbone (67 kDa, 12% acetate incorporation) modified with 0.1 mmol/g N-acrylamidoacetaldehyde dimethyl acetal (NAAADA) pendant polymerizable groups (PVA 888-7X). Hydrophilicity of the PVA macromer can be adjusted by reacting with hydrophobic acetal or hydrophilic ammonium acetal. Macromers can also be modified to enhance the wound dressing tackiness, change the solution viscosity and gellation speed, and to change the wound dressing water content, absorption capability, and mechanical properties.

Crosslinking Initiators:

The macromers are polymerized by redox free radical polymerization using a two part redox system. One part of the system contains a reducing agent such as ferrous salt. Various ferrous salts can be used, such as ferrous gluconate dihydrate, ferrous sulfate, ammonium ferrous sulfate, ferrous lactate dihydrate, or ferrous acetate. The amount of reducing agent used will vary. In one embodiment, the percent range for ferrous salt in the reductant component is 0.06-0.18% or 0.54-1.61 grams in 10 mL. The other part of the composition contains an oxidizing agent such as hydrogen peroxide. The amount of oxidizing agent used will also vary. In one embodiment, the percent range for oxidizing agent in the oxidant component is 0.05-0.12% or 0.36-0.86 grams in 10 mL. Either or both of the redox solutions can contain macromer. The agents react to initiate the polymerization of the macromer to generate a crosslinked hydrogel. Other reducing agents can be used, including but not limited to, iron, titanium trichloride, cysteine, and sodium thiosulfate. Other oxidizing agents that can be used include, but are not limited to, ammonium persulfate, ceric (IV) salt, and t-butyl hydroperoxide.

Stabilizers:

The oxidizing component is stabilized by peroxide stabilizers such as sodium pyrophosphate or organophosphonates (Dequest® 2010 and Dequest® 2060S, Solutia Inc.). Phosphonates are chelants that offer stabilization of peroxide systems. Dequest® 2010 is 1-hydroxy ethylene-1,1-diphosphonic acid. These can be added in amounts as recommended by the manufacturer, generally less than 200 ppm. The reducing component is stabilized using antioxidant stabilizers, including but not limited to ascorbic acid (vitamin C), glutathione, lipoic acid, uric acid, carotenes (vitamin A), and α-tocopherol (vitamin E). Generally the antioxidant stabilizer is added at below 1% by weight. Antioxidants also function to stabilize the macromers by inhibiting polymerization.

Antimicrobial Active Agents:

The dressing functions as a drug delivery matrix to deliver antimicrobial active agents to the wound both immediately and over a period of time after application. Release of the incorporated active agent from the hydrogel to the wound is achieved by diffusion of active agent from the hydrogel. In a preferred embodiment, the antimicrobial active agent is a silver ion releasing compound such as silver chloride.

The silver ion releasing compound is formed in situ on the wound. A silver salt, such as silver acetate, silver lactate, silver laurate, silver sulfate, silver sulfonate, silver fluoride, silver salicylate, silver benzoate, or silver nitrate is included in the oxidant part of the composition. The silver salt is desirably present in an amount of from approximately 0.0005% to 0.2% by weight of the composition, more preferably about 0.001% to 0.005% by weight of the composition. The parts per million (ppm) is the calculated amount of silver ions present from the silver salts. The reductant part of the composition includes a counter molecule to silver ion that precipitates the silver as a substance with low solubility. A preferred molecule is a chloride agent such as calcium chloride. Upon delivery of the two components, some of the silver is immediately released to the wound as silver ions and silver chloride but most of the silver remains in the hydrogel as silver chloride which slowly releases silver ion over time and maintains the antimicrobial activity of the dressing.

In another embodiment, silver nitrate or another silver salt is included in the oxidant formulation and sulfadiazine is in the reductant, resulting in antimicrobial silver sulfadiazine in hydrogel upon delivery.

In a third embodiment, lidocaine or a lidocaine salt (e.g. lidocaine hydrochloride) is added to the reductant part. The lidocaine agent is desirably present in an amount of from approximately 0.1% to 5% by weight of the formulation, more preferably about 0.5% to 2% by weight of the formulation. Upon delivery most lidocaine is rapidly released into the wound to reduce pain.

Other Components:

The composition may additionally contain one or more additives such as stablizers, defoamers, pore forming agents, plasticizers, penetration enhancers, colorants, wettings agents, leveling agents, thickeners, fillers, opacifying agents, and absorbents. Other antimicrobial agents can be included such as chlorhexidene acetate, chlorhexidene gluconate, chlorhexidine hydrochloride, chlorhexidine sulfate, polymyxin, tetracycline, tobramycin, gentamicin, rifampician, bacitracin, neomycin, chloramphenical, oxolinic acid, norfloxacin, nalidix acid, pefloxacin, enoxacin, ciprofloxacin, ampicillin, amoxicillin, piracil, cephalosporins, vancomycin, and bismuth tribromophenate. Other additives can include topical pain relief agents such as lidocaine, ibuprofen, diclofenac, and capsaicin and wound healing factors such as proteins and peptides. The composition may contain various additives including but not limited to glycerol, polyethylene glycol, polypropyl glycol, polybutylene glycol, polyacrylic acid, celluloses, calcium alginate, sucrose, lactose, and fructose, sorbitol, mannitol, zylitol, dextrans, hyaluronic acid, polyacrylamidopropyltrimethyl ammonium chloride, calcium chloride, APOSS (Octaammonium-POSS (polyhedral oligomeric silsesquioxane)), and poly(2-acrylamido-2-methylpropane sulfonic acid). These can be added to the wound dressing to improve the performance of the hydrogel dressing including adhesion, tackiness, and to change the water content, water uptake, and moisture vapor transmission (MVTR).

The composition is steam sterilizable and can be stored or packaged under vacuum or an inert atmosphere of nitrogen or argon in order to prevent oxidation of the reductant initiator component.

Delivery of the Compositions

Appropriate viscosity depends upon the delivery means to be employed. Generally, the composition should have a viscosity lower than about 800 cps, preferably lower than 300 cps, more preferably lower than 200 cps to be delivered via aerosol. Delivery through a pump spray generally requires a lower viscosity, such as less than about 150 cps. Spray without aerosol calls for a viscosity less than about 50 cps.

The composition is delivered to the wound from a spray device or a stream device. The spray device includes a container having a dispenser for spray delivery of the liquid composition. The type of container used is variable, depending upon compatibility with the composition and the spray dispenser and can be glass, plastic, or metal. If the solutions are of a low enough viscosity, a spray delivery may be achieved with simple mechanical forces such as those achieved when depressing the plunger of a syringe by hand through an appropriately designed nozzle.

The composition can also be delivered using a syringe outfitted with a spray head, or a dual spray device outfitted with a spray head and, optionally, a mixing chamber. Generally, any chemical, mechanical or electronic method for propelling the liquid composition as a spray from the container is appropriate. In one embodiment, a compatible liquid or gaseous aerosol propellant is placed in an appropriate container along with the composition and the dispenser includes a valve mechanism that enables atomized spray delivery of the liquid composition.

A device is used having two containers so that the components are kept apart until used. The device can have a single dispenser, such as a spray tip from Nordson Corp. or a device having a double dispenser, e.g. a bar spray tip from Micromedics can be used. If a double dispenser is used, the sprays from the dispensers can be aligned to substantially overlap. A suitable device is described in U.S. Pat. No. 5,989,215, for example. It is also possible, although less preferred, to apply the two solutions sequentially. A mixer may be employed in the case of a single dispenser to mix the two solutions before or during spraying. The device may include a meter so that the quantity of composition can be controlled.

The composition is applied to the wound as a stream or spray using an appropriate delivery device. The composition should be applied to result in a hydrogel having a thickness ranging from about 0.01 to 5 mm, desirably about 0.1 to 3 mm. It may be desirable to apply several layers of the composition to the wound to ensure adequate coverage of the wound. Additionally, multiple dressings may be applied over one another in the event of large area wounds and they ideally should form a cohesive unit dressing.

The dressing can be covered with a secondary dressing, or bandage, if desired to protect the hydrogel or to provide additional moisture absorption, for example. Additionally, gauze may be used to create binding scaffolding to aid in the application of the dressing and to ensure it stays in place.

If desirable, the dressing is removed after a period of time, the wound can be cleaned if desired, and a new dressing can be applied. It may be desirable to apply compositions having different formulations or different active agents to compliment the different stages of wound healing.

The dressings can be used on all types of wounds, with appropriate modification of the formulation, as discussed above. The compositions can be applied to skin, mucous membranes, body cavities, and to internal surfaces of bones and tissues that have been damaged as well as in support of external communicating devices such as orthopedic pins, central ports, and IV lines. The dressings can be used on wounds such as cuts, abrasions, ulcers, surgical incision sites, burns, and to treat other types of tissue damage.

EXAMPLES

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric. The examples are not intended to restrict the scope of the invention.

Experimental Details

Adhesion was measured using a 180 degree peel assessment, ASTM D-330/D3330M-04 (modified), assessed on defatted porcine skin. The hydrogel dressing was cast in specified dimensions between the porcine skin and a gauze strip whereupon it adhered to the porcine skin and impregnated into the weave of the gauze. Once the dressing was fully cured, the gauze was clamped into an Instron with fixtures and clamps designed specifically for the orientation of the peel test. The gauze clamped to the Instron was peeled away from the porcine tissue at 180 degrees until the impregnated dressing contacting the porcine skin experienced adhesion failure between the dressing and the skin. The maximum force required to induce the adhesion failure was recorded.

Tack was measured with fully cured test samples of the wound dressing measuring between 4 and 5 square inches in area and 2.5 mm thick. The dressing was formed inside of a mold, on top of an aluminum heating plate that maintains a surface temperature of 37° C. to simulate body temperature. The test sample and heating plate were placed under a linear tensile tester (Instron or MTS) and tested with a circular aluminum probe of 2 square centimeters attached to the load cell and crosshead. The probe was lowered onto the test article and a pre-load of 0.5N was applied. The crosshead then lifted the probe off the test sample and the force was measured and subsequently evaluated. This test was performed with an N value of 6 and was repeated at predefined time points in order to determine the tack phase.

Moisture Uptake was measured by casting the in-situ curing wound dressing onto a highly absorbent sterile sheet (Texwipe) in known dimensions (diameter and height). The dressing impregnates into the weave of the sheet as it cures, creating a tight bond. The sheet was saturated with 0.9% saline then weighed for zero hour weight. The dressing cast on the sheet was then placed, dressing side up, onto a sponge saturated and floating in a sealable bath of 0.9% saline. The samples were allowed to sit on the saturated sponge in the sealed environment at room temperature for 24 hours. After 24 hours the sample were removed from the sponge. The sheets (not the dressing) were patted dry for free water and the entire assembly (dressing and sheet) was weighed. The 24 weight was recorded and the percent difference was reported as the percent moisture absorbed.

MVTR was measured similarly to the moisture uptake experiment above. The in-situ curing wound dressing was cast onto a permeable sheet in known dimensions (diameter and height). The dressing and impregnated sheet were positioned into an MVTR cup, a cup designed to trap fluid released from substrate to be tested. The cup with the substrate, in this case wound dressing impregnated sheet, was weighed at a zero time point and placed into a conditioned environment of 23° C. and 50% humidity for 24 hours. After 24 hours the cup was weighed again for weigh loss as a result of water vapor escape through the substrate.

Example 1

In Situ Forming Hydrogel with In Situ Forming Silver Chloride

This example demonstrates a typical composition of the in situ forming hydrogel with 250 ppm of antimicrobial silver. Amounts are indicated as percentage by weight. In all of the Examples, the PVA macromer was PVA 888-7X which has a PVA backbone (67 kDa, 12% acetate incorporation) modified with 0.1 mmol/g N-acrylamidoacetaldehyde dimethyl acetal (NAAADA) pendant polymerizable groups.

The components of Part A (the oxidant) were manufactured into a homogeneous solution in large containers. The containers were sealed and purged with medical grade nitrogen gas to replace oxygen and sterilized at 120° C. Once sterile, Part A was ready to be dispensed into the final syringe packaging. The components of Part B (the reductant) were similarly manufactured into a homogenous solution in large containers, with the exception of $CaCl_2$. This component was prepared separately by dissolution in water and then added to the bulk solution of Part B. After mixing together the solutions thoroughly, the container was sealed and sterilized at 120° C. The ingredients are summarized in Table 1. A similar formulation was made with 6% PVA.

TABLE 1

| Part A (oxidant) Ingredient | % by Weight | Part B (reductant) Ingredient | % by Weight |
| --- | --- | --- | --- |
| Polyvinyl alcohol | 8.00 | Polyvinyl alcohol | 8.00 |
| Hydrogen peroxide | 0.07 | Ferrous lactate | 0.11 |
| Glycerol | 10.00 | Glycerol | 10.00 |
| Silver nitrate | 0.04 | Calcium chloride | 0.40 |
| Dequest 2010 | 0.01 | Ascorbic acid | 0.15 |
| Water | 81.98 | Water | 81.34 |
| Total | 100 | Total | 100 |

The results are summarized in Table 2.

TABLE 2

| Formulation | Initial Adhesion (N) | Adhesion @ 4 hours (N) | Tackiness at 4 h (N) | Moisture uptake at 24 h (%) | MVTR (g/m$^2$/24 h) |
| --- | --- | --- | --- | --- | --- |
| Specification | ≥0.03 | 0.5-5 | ≤2.0 | 20-40 | 100-400 |
| 6% PVA | 0.06-0.08 | 1.94-5.18 | 1.36-1.74 | 36.87-43.45 | 250.1-293.7 |
| 8% PVA | 0.33 | 3.66 | 1.5 | 45.6 | 245.46 |

Example 2

Silver Release

Formulations similar to that of Example 1 but with varying amounts of silver nitrate were tested for their silver release kinetics. FIG. 1 shows the release kinetics of the different samples over 7 days. The formulations were prepared as in Example 1 and were made into samples of 3 mm thickness and 4.8 cm in diameter. The samples were placed in 2 mM PBS at room temperature. Sample 1 with 50 ppm silver nitrate was placed in PBS with a weight ratio of hydrogel dressing to PBS solution 1:66. Sample 2 with 150 ppm silver nitrate was placed in PBS with a weight ratio of 1:142 and a third sample analogous to sample 2, but without $CaCl_2$ was placed in PBS with a ratio of 1:142. The silver content in release solution was determined with ICP-AES (Inductive Coupled Plasma Atomic Emission Spectrometry).

Lower silver loading (sample 1-50 ppm) resulted in a faster release. We assume that the relatively faster release compared to 150 ppm is due to the faster dissolution and diffusion rate of the smaller particles of AgCl formed at lower concentration. Release from sample 3 (not containing $CaCl_2$) was slowest. The hydrogel immediately turned to brown, presumably because the silver was reduced to metallic silver in the absence of calcium chloride and was therefore released more slowly.

Example 3

Zone of Inhibition Over 72 Hours

Figure 2:
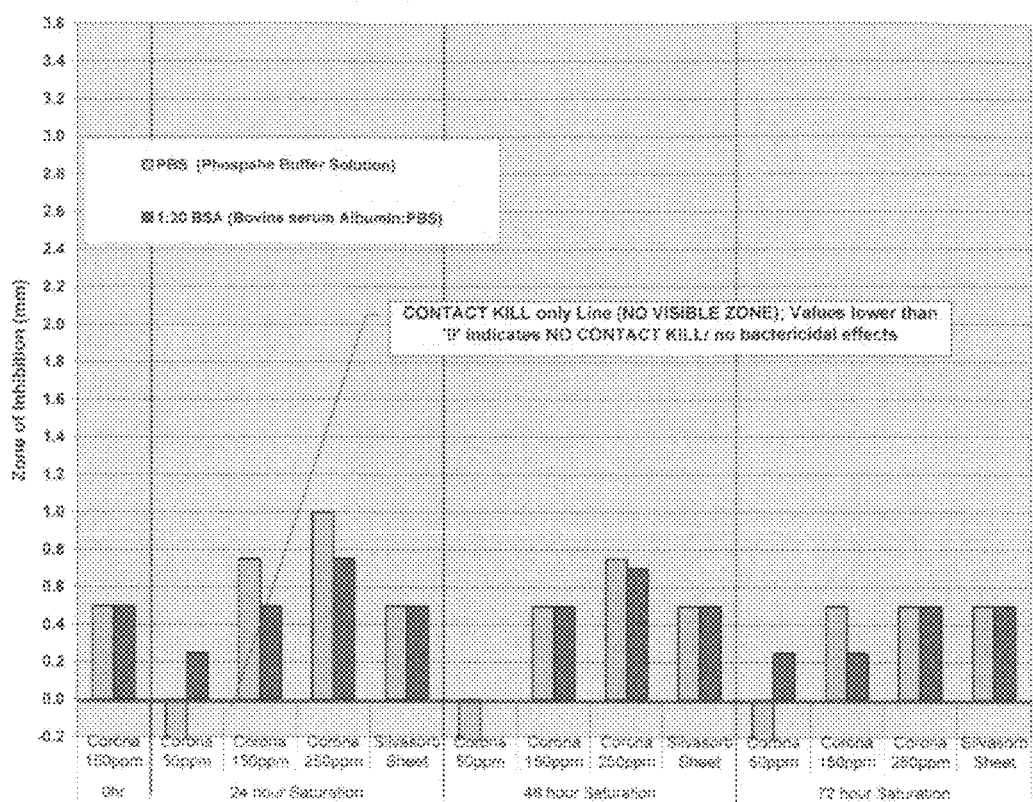
FIG. 2 illustrates the zone of inhibition of an embodiment of the wound dressing against *Staphylococcus aureus* at 24, 48, and 72 hours.
Figure 3:
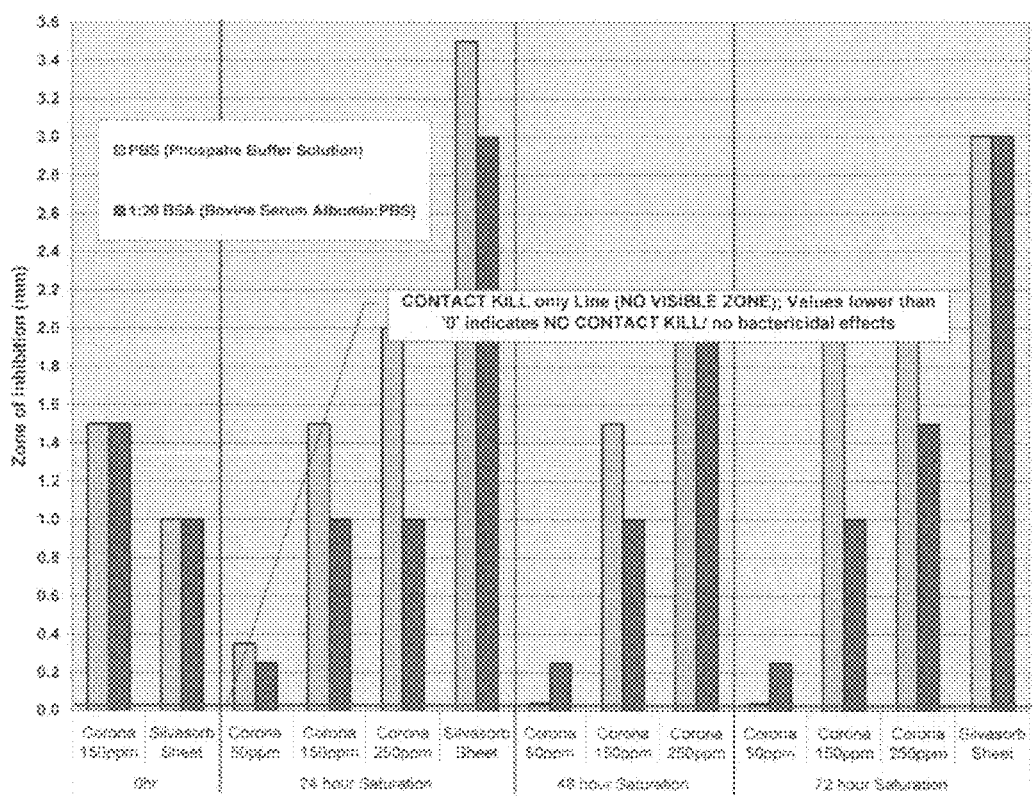
FIG. 3 illustrates the zone of inhibition of an embodiment of the wound dressing against *Pseudomonas aeruginosa* at 24, 28, and 72 hours.

The slow release of silver ions over 24, 48, and 72 hours was also demonstrated experimentally by saturating wound dressing formulations in 0.9% saline and also in 1:20 BSA solution (Bovine Serum Albumin: Phosphate Buffer Solution). Sample specimens of wound dressing to be tested were prepared as in Example 1 above with silver concentrations of 50, 150 and 250 ppm. Sterilized parts A and B were loaded into steam sterilized double barrel delivery syringes having a 12 element static mixing tip. Parts A and B were delivered onto a Teflon sheet wiped thoroughly with 70% IPA; only enough material was delivered to create multiple drops of cured hydrogel on the Teflon sheet. Rough dimensions of the drops were 1 cm diameter by 0.2-0.3 cm thick. Samples were tested for zone of inhibition analysis at zero hour (no fluid exposure), 24, 48, and 72 hours. The 24, 48, and 72 hour samples were placed in sterile containers, covered with solution (2 ml), sealed and placed in a 37 degree Celsius chamber on orbital shaker set at 60 hertz. Saturation solutions were changed at 24 hour increments until the desired time point was reached. At 24, 48, and 72 hours, the samples were removed from the saturation fluids and tested for a Zone of Inhibition performance against *Staphylococcus aureus* (FIG. 2) and *Pseudomonas aeruginosa* (FIG. 3) bacteria. Bacterial concentrations ranged between $10^6$ to $10^7$ CFU/ml. Zone of Inhibition results indicate that the formulations above 150 ppm silver ions retained their antimicrobial activity over 72 hours. The 250 ppm silver ion formulation exhibited an inhibition zone performance of 0.5 mm and 1.5 mm against $10^6$ bacterial colonies of *Staphylococcus aureus* and *Pseudomonas aeruginosa* respectively after 72 hours of saturation in 1:20 BSA solution. FIGS. 2 and 3 illustrate the results.

Example 4

In Situ Forming Hydrogel with In Situ Forming Silver Sulfadiazine

This example demonstrates a composition of the in situ forming hydrogel with in situ forming silver sulfadiazine. Amounts are indicated as percentage by weight in Table 3.

TABLE 3

| Part A Ingredient | % by Weight | Part B Ingredient | % by Weight |
| --- | --- | --- | --- |
| Polyvinyl alcohol | 6.00 | Polyvinyl alcohol | 6.00 |
| Hydrogen peroxide | 0.07 | Ferrous ammonium sulfate | 0.11 |
| Glycerol | 10.00 | Glycerol | 10.00 |
| Silver nitrate | 0.04 | Sulfadiazine | 0.8 |
| Dequest | 0.01 | Ascorbic acid | 0.15 |
| Water | 83.98 | Water | 83.68 |
| Total | 100 | Total | 100 |

Example 5

In Situ Forming Hydrogel with In Situ Forming Silver Chloride and Lidocaine

This example demonstrates a composition of the in situ forming hydrogel with a combination of active drugs. The mixing procedures for Part A and B were performed according to Example 1. The Lidocaine HCl was added last to Part B. The final concentration of Lidocaine HCl in the crosslinked gel was 2 wt %. The formulation is summarized in Table 4.

TABLE 4

| Part A Ingredient | % by Weight | Part B Ingredient | % by Weight |
| --- | --- | --- | --- |
| Polyvinyl alcohol | 8.00 | Polyvinyl alcohol | 8.00 |
| Hydrogen peroxide | 0.07 | Ferrous ammonium sulfate | 0.11 |
| Glycerol | 10.00 | Glycerol | 10.00 |
| Silver nitrate | 0.04 | Calcium chloride | 0.40 |
| Dequest 2010 | 0.01 | Ascorbic acid | 0.15 |
|  |  | Lidocaine HCl | 4.00 |
| Water | 81.98 | Water | 77.34 |
| Total | 100 | Total | 100 |

Example 6

Addition of Various Additives

In this Example, various additives were tested for their effect upon the hydrogel wound dressing. An antibiotic was not added to these samples. The base hydrogel was made as in Example 1, with the deletion of silver nitrate. Other samples were made as follows: 10% APOSS-10% Octaammonium-POSS (polyhedral oligomeric silsesquioxane) was added to both parts A and B; 10% glycerol-10% glycerol was added to both parts A and B; positively charged PVA-8% Nelfilcon B (a PVA-based macromer having a molecular weight of 68,000 and 7 crosslink density) having quaternary amines was added to both parts A and B; Pluronics F127—0.5% Pluronics F127 was added to both parts A and B; Pluronics Triblock—2.5% PEO-PPO-PEO Mw=1900 was added to both parts A and B. The results are shown in Table 5.

TABLE 5

| Formulation | Initial Adhesion (N) | Tackiness at 4 h (N) | Moisture uptake at 24 h (%) | MVTR ($g/m^2/24$ h) |
| --- | --- | --- | --- | --- |
| Base Hydrogel | 0.587 ± 0.1 | 0.39 | 39 | 233 |
| 10% APOSS | 0.33 ± 0.2 | 0.19 | 34 | 444 |
| 20% Glycerol | 0.33 ± 0.05 | 0.09 | 37 | 248 |
| Positively charged PVA | 0.34 ± 0.08 | 0.10 | 3 | 253 |
| Pluronics F 127 | 0.36 ± 0.05 | 0.21 | 27 | 318 |
| Pluronics Triblock | 0.29 ± 0.2 | 0.35 | 36 | 248 |

The addition of 10% APOSS, 20% glycerol, or positively charged PVA to the base hydrogel decreased the initial and long term adhesion of the hydrogel to the porcine substrate. The addition of 20% glycerol performed poorly long term as the high concentration of glycerol leached to the surfaces of the hydrogel causing adhesion failure after 8 to 12 hours. The inclusion of APOSS did not significantly affect the adhesion or the tack of the hydrogel but does pose potential cytotoxicity issues. Positively charged PVA had over 40% adhesion loss from the same PVA concentration formulation using neutral PVA; the tack profile however performed more favorably.

Tack and the length of the tack phase were decreased with the addition of 20% glycerol and with the use of positively charged PVA. The addition of 20% glycerol decreased the highest tack value when compared to a 10% glycerol dressing by greater than 20%; whereas positively charged PVA in place of neutral PVA performed the best in regards to tack by decreasing the highest tack value by over 50% and decreasing the tack phase from 4 hours to 2 hours. However, as the tack was decreased the adhesion was also decreased.

Adding 10% APOSS to the hydrogel increased the MVTR from 233 to 444 $g/m^2/24$ hr, which suggests APOSS encourages a more efficient transport of water vapor across the hydrogel matrix. The moisture uptake was not significantly affected by increasing the glycerol from 10% to 20%, adding 10% APOSS, or using positively charged PVA in place of neutral PVA.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A composition for forming an antimicrobial hydrogel wound dressing in situ on a wound wherein the dressing exhibits both immediate and extended antimicrobial release, comprising two parts, wherein at least one of the parts includes a macromer which forms a hydrogel when the two parts are combined, and wherein one of the parts includes a first compound that will release an antimicrobial agent upon formation of the hydrogel and the second part includes a second compound that complexes with the antimicrobial agent when the two parts are combined to form a complex that slowly releases the antimicrobial agent, wherein the first compound is a silver salt and the second compound includes a counterion or compound that forms a silver salt having low solubility.

2. The composition of claim 1, wherein the first compound is silver nitrate and the counterion is chloride or iodide.

3. The composition of claim 1, wherein the first compound is silver nitrate and the second compound is calcium chloride.

4. The composition of claim 1, wherein the first compound is silver nitrate and the second compound is sulfadiazine.

5. The composition of claim 1, further comprising a second antimicrobial agent, pain relief agent, or would healing factor.

6. The composition of claim 1, wherein the antimicrobial wound dressing exhibits antimicrobial activity for up to 36 hours.

7. An antimicrobial wound dressing formed in situ on a wound, comprising a hydro gel and an antimicrobial agent, wherein the antimicrobial agent has antimicrobial activity upon in situ formation of the dressing on the wound and over an extended period of time.

8. A method of making an antimicrobial dressing in situ on a wound, wherein the dressing exhibits both immediate and extended antimicrobial release, comprising the steps of delivering a composition that forms a hydrogel wound dressing in situ to the wound and delivering a first compound that will release an antimicrobial antimicrobial agent upon formation of the hydrogel and a second compound that complexes with the antimicrobial agent when the two parts are combined to form a complex that slowly releases the antimicrobial agent, wherein the first compound is a silver salt and the second compound includes a counterion or compound that forms a silver salt having low solubility.

9. The method of claim 8, wherein the method involves precipitating silver chloride in situ.

\* \* \* \* \*